United States Patent [19]

Ernst et al.

[11] Patent Number: 4,567,261
[45] Date of Patent: Jan. 28, 1986

[54] PREPARATION OF RIBOFLAVIN

[75] Inventors: Hansgeorg Ernst, Ludwigshafen; Wolfram Schmidt, Friedelsheim; Joachim Paust, Neuhofen, all of Fed. Rep. of Germany

[73] Assignee: BASF Aktiengesellschaft, Fed. Rep. of Germany

[21] Appl. No.: 570,457

[22] Filed: Jan. 13, 1984

[30] Foreign Application Priority Data

Jan. 26, 1983 [DE] Fed. Rep. of Germany ....... 3302497

[51] Int. Cl.[4] ......................................... C07D 475/14
[52] U.S. Cl. ................................................... 544/251
[58] Field of Search ........................................ 544/251

[56] References Cited

U.S. PATENT DOCUMENTS

| 2,155,555 | 4/1939 | Karrer | 544/251 |
| 2,807,611 | 9/1957 | Howe | 544/251 |
| 2,847,413 | 8/1958 | Folkers et al. | 544/251 |

OTHER PUBLICATIONS

Fatty Acids and Their Industrial Applications, ed. Pattison, Marcel Dekker, Inc., New York, (1968), pp. 366–368.
Berezouskii, et al., Chemical Abstracts, vol. 57, 1962, 11290i–11291a.
Tishler, et al., J. Am. Chem. Soc., 69, (1947), pp. 1487–1492.
Berezouskii, et al., J. Am. Chem. Soc., USSR 1961, pp. 3444–3448.
Haley, et al., J. Am. Chem. Soc., 76, (1954), pp. 2926–2929.

Primary Examiner—Donald G. Daus
Assistant Examiner—Diana G. Rivers
Attorney, Agent, or Firm—Keil & Weinkauf

[57] ABSTRACT

Riboflavin of the formula I

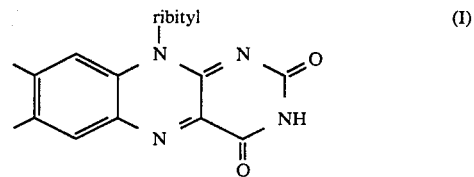

is prepared by condensing a 4,5-dimethyl-N-(D)-ribityl-2-phenylazoaniline of the formula II

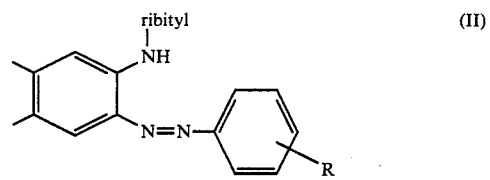

where R is H or —Cl, —NO$_2$ or —CH$_3$ in the o- or p-position, with barbituric acid of the formula III

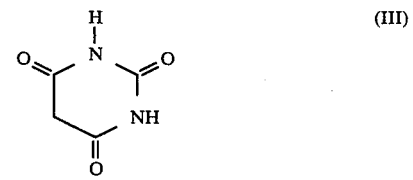

in the presence of an acid as the condensing agent, by an improved process in which the acidic condensing agent used is an aliphatic or cycloaliphatic/aliphatic tertiary carboxylic acid of the general formula IV

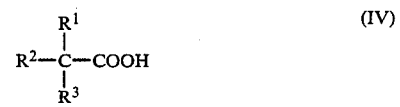

where $R^1$, $R^2$ and $R^3$ are each a lower alkyl group, $R^1$, $R^2$ and $R^3$ together containing 3 to 20, preferably 3 to 10, carbon atoms, or $R^1$ is a lower alkyl group, in particular methyl, and $R^2$ and $R^3$ together form a tetramethylene or pentamethylene group.

The process can be particularly advantageously carried out using trimethylacetic acid or a commercial mixture of saturated tertiary carboxylic acids, e.g. Versatic $^R$10-acid.

7 Claims, No Drawings

PREPARATION OF RIBOFLAVIN

The present invention relates to an improved process for the preparation of riboflavin (I; vitamin $B_2$) by condensing a 4,5-dimethyl-N-(D)-ribityl-2-phenylazoaniline (II) with barbituric acid (III) in the presence of an acid as a condensing agent.

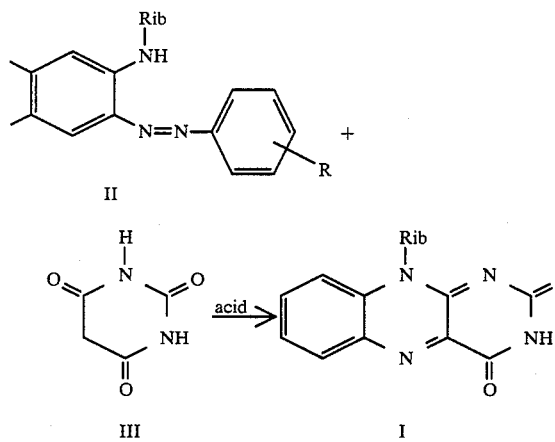

Rib = ribityl
R = H or a p- or o-substituent, eg. $-Cl$, $-NO_2$ or $-CH_3$.

Apart from the improvement according to the invention, this final step of the riboflavin synthesis has been disclosed in several publications, for example in the paper by Tishler et al (J.Am.Chem.Soc., 69 (1947), 1487), in which glacial acetic acid was used as the acidic condensing agent.

Furthermore, Berezowskii et al (J.Gen.Chem. USSR 1961, 3444) investigated a number of other acids with regard to their suitability as condensing agents. According to these authors, the best yields of I (about 70%) were obtained using acetic acid, phenylacetic acid and benzoic acid. However, an excess of barbituric acid of 65 mole% was used. If, on the other hand, II and III are employed in equimolar amounts, the yield of I decreases substantially. For example, Haley et al (J.Am.Chem.Soc., 76 (1954), 2926) obtained a yield of riboflavin of only 41% when glacial acetic acid was used as the condensing agent and II and III were reacted in a molar ratio of 1:1.

It is an object of the present invention to improve the unsatisfactory yields of I and furthermore to dispense with the use of a molar excess of III over II.

We have found that this object is achieved, and that substantially higher yields of riboflavin are obtained in the condensation reaction described at the outset, if the acidic condensing agent used in an aliphatic or cycloaliphatic/aliphatic tertiary carboxylic acid of the general formula IV

where $R^1$, $R^2$ and $R^3$ are each a lower alkyl group, $R^1$, $R^2$ and $R^3$ together containing 3 to 20, preferably 3 to 10, carbon atoms, or $R^1$ is a lower alkyl group, in particular methyl, and $R^2$ and $R^3$ together form a tetramethylene or pentamethylene group.

Examples of suitable tertiary carboxylic acids of the general formula IV are tertiary aliphatic carboxylic acids, such as trimethylacetic acid (pivalic acid), 2,2-dimethylbutyric acid and 2,2-dimethylpentanoic acid, tertiary cycloaliphatic/aliphatic carboxylic acids, such as 1-methylcyclohexane-1-carboxylic acid or 1-methylcyclopentanecarboxylic acid, or mixtures of tertiary carboxylic acids.

For the purposes of the present invention, particularly suitable mixtures of tertiary carboxylic acids are commercially available mixtures of synthetic acids which essentially contain saturated tertiary carboxylic acids of the formula IV. Particular examples are Versatic ®10-acid, which is a synthetic $C_{10}$-carboxylic acid from Shell Chemie and similar products from Esso, which are available commercially under the name Neo acids. Examples of these are neopentanoic acid, which contains trimethylacetic acid as the principal component, and neodecanoic acid, which probably has a composition similar to that of Versatic 10-acid. Particularly good results are achieved using trimethylacetic acid or Versatic ®10-acid, the latter being preferred because of its better properties in respect of odor and because, being a liquid, it is easier to handle.

Starting compounds II and their preparation are known. In general, the cheapest compound from this series, ie. the phenylazo derivative, is used. In principle, however, it is also possible to use compounds in which the phenylazo group is substituted in the ortho-position or, in particular, the para-position by substituents, such as methyl, chlorine or nitro. The starting compounds need not be specially purified, but can be used as crude products. The yields are then based on II contained in the starting material.

Advantageously, the reaction is carried out in the presence of an inert diluent or solvent, this being the conventional procedure.

Preferred solvents are those in which the water formed in the condensation is also completely or partially soluble, ie. dioxane, tetrahydrofuran, dimethylformamide and in particular the relatively cheap lower alcohols having a boiling point from 80° to 150° C., eg. propanol, isopropanol, n-butanol, isobutanol and n-pentanol, in particular isobutanol.

Advantageously, the amount of solvent should be just sufficient to dissolve the starting compounds, and is in general from 2 to 12 liters per kg of II. After the mixture has been heated for a short time, the riboflavin formed begins to crystallize out.

The amount of carboxylic acid is preferably from 0.5 to 6 moles per mole of II; for example, this corresponds to about 0.19–1.7 kg per kg of II in the case of pivalic acid, and to 236 g–2.85 kg per kg of II in the case of Versatic 10-acid.

A particular advantage of the novel process is that, even when equimolar amounts of II and III are used, the yields obtained are substantially higher than those obtained hitherto. These yields are about 80%, but can be increased to above 90% if as much as a 0.15 molar excess of III is used. Although a larger excess does not have an adverse effect, it does not result in any noticeable increase in yield (cf. Examples 3a and b).

The reaction temperatures are from 80° to 120° C. Preferably, the reaction is carried out at above 100° C., ie. at about 100°–115° C., and in an appropriately highboiling solvent, especially isobutanol. At 100° C., the reaction time is about 5-15 hours.

If the reaction is carried out in an alcohol, such as isobutanol, as the solvent, the acids according to the invention, in contrast to acetic acid which in particular has been conventionally used to date, have the advantage that they hardly tend to undergo esterification, so that scarcely any loss of the solvent and acid result and the cost of regenerating these is saved.

The reaction mixture can be worked up by a conventional method, for example by allowing it to cool and filtering off the riboflavin which has crystallized out.

EXAMPLES 1 AND 2 AND COMARATIVE EXAMPLES 1 TO 7

A mixture of 40 g (0.111 mole) of 4,5-dimethyl-N-(D)-ribityl-2-phenylazoaniline, 14.2 g (0.111 mole) of barbituric acid and 30 g (0.295 mole) of pivalic acid in 190 ml of isobutanol was stirred under reflux at 105°-110° C. for 10 hours, after which it was cooled to room temperature. The riboflavin precipitated was filtered off, washed with methanol, cold water and hot water, and dried under reduced pressure at 60° C.

For comparison, the reaction was repeated with, in each case, 0.295 mole of some other acids as the condensing agent, other conditions being identical. The results are shown in the Table below. The purity of the riboflavin was determined by UV measurement in accordance with the European pharmacopeia.

TABLE

| Examples | | Condensing agent | Yield of riboflavin (%) | Purity (%) | Yield based on pure substance (%) |
|---|---|---|---|---|---|
| (a) | According to the invention | | | | |
| | 1 | pivalic acid | 78.6 | 98.2 | 77.2 |
| | 2 | Versatic 10-acid | 79.9 | 96.5 | 77.1 |
| (b) | for comparison | | | | |
| | 1 | acetic acid | 74.2 | 94.7 | 70.3 |
| | 2 | propionic acid | 73.9 | 95.5 | 70.6 |
| | 3 | n-butyric acid | 75.8 | 93.6 | 70.9 |
| | 4 | isobutyric acid | 74.6 | 93.2 | 69.5 |
| | 5 | n-valeric acid | 73.9 | 94.6 | 69.9 |
| | 6 | isovaleric acid | 75.9 | 92.3 | 70.0 |
| | 7 | hexanoic acid | 73.4 | 93.4 | 68.6 |

EXAMPLE 3

(a) When the conditions described in Example 1 were employed but, instead of 14.2 g (0.111 mole) of barbituric acid, an 11% excess, ie. 15.8 g (0.123 mole), was used, 36.5 g (87.5% of theory) of 96.2% pure riboflavin were obtained, the purity being determined by means of a UV measurement.

(b) When the conditions described in Example 1 were employed but a 26% excess, ie. 17.9 g (0.14 mole), of barbituric acid was used, 36.2 g (86.8% of theory) of 95.5% pure riboflavin were obtained.

EXAMPLE 4

36 g (0.1 mole) of 4,5-dimethyl-N-(D)-ribityl-2-phenylazoaniline and 14.2 g (0.111 mole) of barbituric acid in a mixture of 170 ml of isobutanol and 73.5 ml (0.393 mole) of Versatic 10-acid were stirred under reflux for 10 hours, after which the reaction mixture was allowed to cool to room temperature. The precipitate was filtered off, washed with methanol, cold water and then hot water, and dried under reduced pressure at +60° C. 34.9 g (92.8% of theory) of 95.6% pure riboflavin were obtained, the purity being determined by means of a UV measurement.

EXAMPLE 5

40 g (0.111 mole) of 4,5-dimethyl-N-(D)-ribityl-2-phenylazoaniline and 15.8 g (0.123 mole) of barbituric acid in a mixture of 190 ml of isobutanol with 80 ml (0.428 mole) of Versatic 10-acid were stirred under reflux for 10 hours, after which the reaction mixture was allowed to cool to room temperature. The precipitate was washed with methanol, cold water and then hot water, and dried under reduced pressure at +60° C. 38.8 g (93% of theory) of 95.6% pure riboflavin were obtained.

EXAMPLE 6

36 g (0.1 mole) of 4,5-dimethyl-N-(D)-ribityl-2-phenylazoaniline and 14.85 g (0.116 mole) of barbituric acid in a mixture of 170 ml of isobutanol and 60 ml (0.532 mole) of pivalic acid were refluxed for 6 hours. The mixture was worked up as described in Example 4 to give 33.1 g (88.0% of theory) of 98.3% pure riboflavin.

EXAMPLE 7

36 g (0.1 mole) of 4,5-dimethyl-N-(d)-ribityl-2-phenylazoaniline and 14.2 g (0.111 mole) of barbituric acid in a mixture of 170 ml of n-pentanol and 30 ml (0.266 mole) of pivalic acid were stirred at 115° C. for 10 hours. After the mixture had cooled to room temperature, it was worked up as described in Example 4 to give 32.9 g (87.5% of theory) of 95.5% pure riboflavin.

EXAMPLE 8

40 g (0.111 mole) of 4,5-dimethyl-N-(D)-ribityl-2-phenylazoaniline and 15.8 g (0.123 mole) of barbituric acid in a mixture of 120 ml of isobutanol and 98 ml (0.532 mole) of Versatic 10-acid were stirred under reflux for 6 hours. The mixture was worked up as described in Example 4 to give 39.6 g (94.9% of theory) of 93.4% pure riboflavin.

EXAMPLE 9

33.6 g (93.6 millimoles) of 4,5-dimethyl-N-(D)-ribityl-2-phenylazoaniline and 13.7 g (107 millimoles) of barbituric acid in a mixture of 170 ml of isobutanol and 98 ml of Neo-Acid (from Esso) were stirred under reflux for 10 hours, after which the reaction mixture was allowed to cool to room temperature. The precipitate was washed with methanol, cold water and then hot water, and dried under reduced pressure at +70° C. 33.4 g (94.9%) of 94% pure riboflavin were obtained, the purity being determined in accordance with the European pharmacopeia.

EXAMPLE 10

36.0 g (0.1 mole) of 4,5-dimethyl-N-(D)-ribityl-2-phenylazoaniline and 14.7 g (0.115 mole) of barbituric acid in a mixture of 120 ml of dioxane and 98 ml of Versatic 10-acid were stirred under reflux for 10 hours. The mixture was worked up as described in Example 4 to give 37.7 g of 96% pure riboflavin. The crude yield was quantitative.

EXAMPLE 11

36.0 g (0.1 mole) of 4,5-dimethyl-N-(D)-ribityl-2-phenylazoaniline and 14.7 g (0.115 mole) of barbituric acid in a mixture of 170 ml of dioxane and 60 ml of pivalic acid were stirred under reflux for 10 hours. The mixture was worked up as described in Example 4 to give 36.5 g (97.0%) of 97% pure riboflavin, the purity being determined in accordance with the European pharmacopeia.

EXAMPLE 12

33.6 g (93.6 millimoles) of 4,5-dimethyl-N-(D)-ribityl-2-phenylazoaniline and 13.7 g (107 millimoles) of barbituric acid in a mixture of 120 ml of 1,2-dimethoxyethane and 105 ml of Versatic 10-acid were stirred under reflux for 14 hours. The mixture was worked up as described in Example 4 to give 33.5 g (95.2%) of 95% pure riboflavin, the purity being determined in accordance with the European pharmacopeia.

We claim:

1. An improved process for the preparation of riboflavin of the formula I

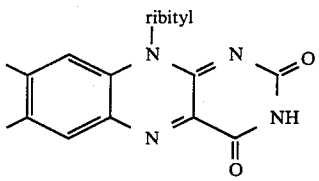

by condensing a 4,5-dimethyl-N-(D)-ribityl-2-phenylazoaniline of the formula II

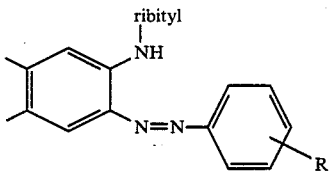

where R is H or —Cl, —NO$_2$ or —CH$_3$ in the o- or p-position, with barbituric acid of the formula III

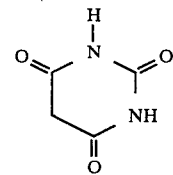

in the presence of an acid as a condensing agent, wherein the acidic condensing agent used is an aliphatic or cycloaliphatic/aliphatic tertiary carboxylic acid of the formula IV

where $R^1$, $R^2$ and $R^3$ are each a lower alkyl group, $R^1$, $R^2$ and $R^3$ together containing 3 to 20, carbon atoms, and $R^2$ and $R^3$ together form a tetramethylene or pentamethylene group.

2. A process for the preparation of riboflavin as claimed in claim 1, wherein the acidic condensing agent used is trimethylacetic acid.

3. A process for the preparation of riboflavin as claimed in claim 1 wherein the acidic condensing agent used is Versatic ®10-acid.

4. An improved process for the preparation of riboflavin as claimed in claim 1, wherein the molar ratio of the 4,5-dimethyl-N-(D)-ribityl-2-phenylazoaniline of the formula II to barbituric acid III is from 1:1 to 1:1.15.

5. An improved process for the preparation of riboflavin as claimed in claim 1, wherein the condensation is carried out in isobutanol as the solvent.

6. A process in accordance with claim 1, wherein the $R^1$, $R^2$ and $R^3$ substituents of formula IV together contain from 3 to 10 carbon atoms.

7. A process in accordance with claim 1, wherein the $R^1$ substituent of formula IV is a methyl radical.

* * * * *